United States Patent
Roever et al.

(10) Patent No.: US 8,227,491 B2
(45) Date of Patent: Jul. 24, 2012

(54) 5-(3,4-DICHLORO-PHENYL)-N-(2-HYDROXY-CYCLOHEXYL)-6-(2,2,2-TRIFLUORO-ETHOXY)-NICOTINAMIDE AND SALTS THEREOF

(75) Inventors: Stephan Roever, Inzlingen (DE); Matthew Wright, Basel (CH)

(73) Assignee: Hoffmann-La Roche Inc., Nutley, NJ (US)

(*) Notice: Subject to any disclaimer, the term of this patent is extended or adjusted under 35 U.S.C. 154(b) by 161 days.

(21) Appl. No.: 12/875,196

(22) Filed: Sep. 3, 2010

(65) Prior Publication Data

US 2011/0065759 A1    Mar. 17, 2011

(30) Foreign Application Priority Data

Sep. 11, 2009  (EP) ..................... 09170097

(51) Int. Cl.
*A61K 31/44* (2006.01)
*C07D 213/02* (2006.01)

(52) U.S. Cl. ......... 514/350; 546/290; 546/298; 514/345

(58) Field of Classification Search .................. 546/290, 546/298; 514/345, 350
See application file for complete search history.

(56) References Cited

U.S. PATENT DOCUMENTS 7,812,028 B2 * 10/2010 Andjelkovic et al. .... 514/255.06

FOREIGN PATENT DOCUMENTS

WO    2006/106054    10/2006
WO    2008/040651    4/2008

OTHER PUBLICATIONS

International Search Report, dated Oct. 19, 2010, issued in PCT/EP2010/063136.

* cited by examiner

*Primary Examiner* — Golam M M Shameem
(74) *Attorney, Agent, or Firm* — George W. Johnston; Patricia S. Rocha-Tramaloni; Gene J. Yao

(57) ABSTRACT

The present invention relates to a compound of formula I,

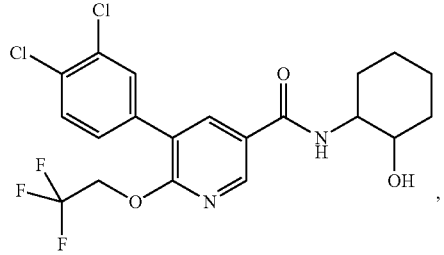

in all its isomeric forms and pharmaceutically acceptable salts thereof, their manufacture, pharmaceutical compositions containing them and their use as medicaments for the treatment and/or prophylaxis of diseases which can be treated with HDL-cholesterol raising agents, such as dyslipidemia, atherosclerosis and cardiovascular diseases.

4 Claims, No Drawings

5-(3,4-DICHLORO-PHENYL)-N-(2-HYDROXY-CYCLOHEXYL)-6-(2,2,2-TRIFLUORO-ETHOXY)-NICOTINAMIDE AND SALTS THEREOF

PRIORITY TO RELATED APPLICATION(S)

This application claims the benefit of European Patent Application No. 09170097.1, filed Sep. 11, 2009, which is hereby incorporated by reference in its entirety.

FIELD OF THE INVENTION

The present invention relates to a compound of formula I,

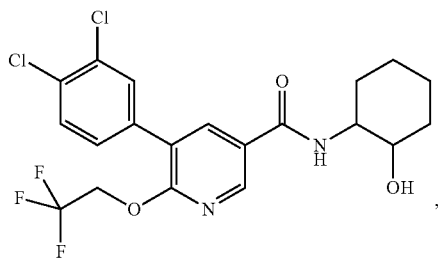

and its isomeric forms and pharmaceutically acceptable salts thereof, their manufacture, pharmaceutical compositions containing them and their use as medicaments. The compound of formula I, its isomeric forms and pharmaceutically acceptable salts are especially useful as HDL-cholesterol raising agents.

BACKGROUND OF THE INVENTION

Atherosclerosis and its associated coronary heart disease is the leading cause of death in the industrialized world. Risk for development of coronary heart disease has been shown to be strongly correlated with certain plasma lipid levels. Lipids are transported in the blood by lipoproteins. The general structure of lipoproteins is a core of neutral lipids (triglyceride and cholesterol ester) and an envelope of polar lipids (phospholipids and non esterified cholesterol). There are 3 different classes of plasma lipoproteins with different core lipid content: the low density lipoprotein (LDL) which is cholesteryl ester (CE) rich; high density lipoprotein (HDL) which is also cholesteryl ester (CE) rich; and the very low density lipoprotein (VLDL) which is triglyceride (TG) rich. The different lipoproteins can be separated based on their different flotation density or size.

High LDL-cholesterol (LDL-C) and triglyceride levels are positively correlated, while high levels of HDL-cholesterol (HDL-C) are negatively correlated with the risk for developing cardiovascular diseases.

No wholly satisfactory HDL-elevating therapies exist. Niacin can significantly increase HDL, but has serious toleration issues which reduce compliance. Fibrates and the HMG CoA reductase inhibitors raise HDL-cholesterol only modestly (~10-12%). As a result, there is a significant unmet medical need for a well tolerated agent which can significantly elevate plasma HDL levels.

Thus, HDL-cholesterol raising agents can be useful as medicaments for the treatment and/or prophylaxis of atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia.

In addition, HDL-cholesterol raising agents may be used in combination with another compound, said compound being an HMG-CoA reductase inhibitor, an microsomal triglyceride transfer protein (MTP)/ApoB secretion inhibitor, a PPAR activator, a bile acid reuptake inhibitor, a cholesteryl ester transfer protein (CETP) inhibitor, a cholesterol absorption inhibitor, a cholesterol synthesis inhibitor, a fibrate, niacin, preparations containing niacin or other HM74a agonists, an ion-exchange resin, an antioxidant, an ACAT inhibitor or a bile acid sequestrant.

SUMMARY OF THE INVENTION

The present invention provides a compound of formula I,

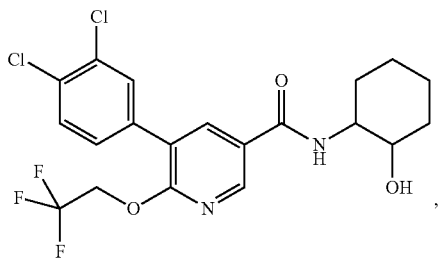

or an isomeric form or pharmaceutically acceptable salt thereof.

The present invention also provides pharmaceutical composition comprising a compound according to claim 1 and a pharmaceutically acceptable carrier and/or an adjuvant.

DETAILED DESCRIPTION OF THE INVENTION

As stated above, the present invention provides a compound of formula I,

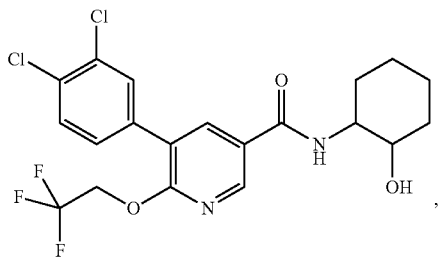

or an isomeric form or pharmaceutically acceptable salt thereof.

The compound is a potent HDL-cholesterol raising agent. It has been found that the compound of formula I of the present invention is very useful for the treatment and/or prophylaxis of diseases which can be treated with HDL-cholesterol raising agents, i.e. the compound of formula I is especially useful for the treatment and/or prevention of dyslipidemia, atherosclerosis and cardiovascular diseases. Object of the present invention is also to provide a compound which is, at therapeutically active concentrations that increase HDL-concentrations, not interacting with the CB1 receptor. This is because CB1 receptor ligands may compromise the therapeutic utility of HDL-cholesterol raising agents, as both agonists and antagonists of the CB1 receptor have the potential to lead to side effects.

Compounds with common structural elements have been disclosed as CB1 receptor antagonists (WO 2006/106054) and mixed CB1 receptor antagonists/HDL cholesterol raising agents (WO 2008/040651).

Unless otherwise indicated, the following definitions are set forth to illustrate and define the meaning and scope of the various terms used to describe the invention herein.

"Isomeric forms" are all forms of a compound characterized by having an identical molecular formula but that differ in the nature or the sequence of bonding of their atoms or in the arrangement of their atoms in space. Preferably, the isomeric forms differ in the arrangement of their atoms in space and can also be termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four non-identical substituents is termed a "chiral center".

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as formic acid, acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. Thus, preferred "pharmaceutically acceptable salts" include the acetate, bromide, chloride, formate, fumarate, maleate, mesylate, nitrate, oxalate, phosphate, sulfate, tartrate and tosylate salt of compounds of formula I. In addition, pharmaceutically acceptable salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, diethylamine, lysine, arginine, N-ethylpiperidine, piperidine, piperazine and the like. The compound of formula I can also be present in the form of zwitterions or in the form of hydrates. Particularly preferred pharmaceutically acceptable salts of compounds of formula I are the hydrochloride salts.

In a preferred aspect, the present invention relates to 5-(3,4-dichloro-phenyl)-N-((1R,2R)-2-hydroxy-cyclohexyl)-6-(2,2,2-trifluoro-ethoxy)-nicotinamide, i.e. a compound of formula I of the isomeric form Ia.

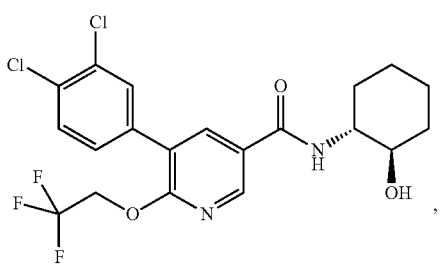

The invention also refers to 5-(3,4-dichloro-phenyl)-N-((1R,2R)-2-hydroxy-cyclohexyl)-6-(2,2,2-trifluoro-ethoxy)-nicotinamide and pharmaceutically acceptable salts thereof.

In another preferred aspect, the present invention refers to 5-(3,4-Dichloro-phenyl)-N-((1S,2R)-2-hydroxy-cyclohexyl)-6-(2,2,2-trifluoro-ethoxy)-nicotinamide, i.e. a compound of formula I of the isomeric form Ib.

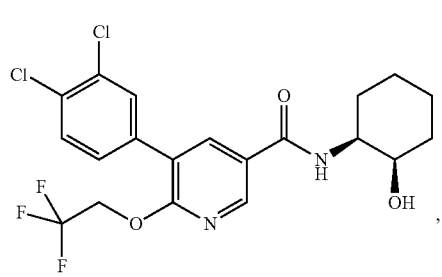

The invention also relates to 5-(3,4-dichloro-phenyl)-N-((1S,2R)-2-hydroxy-cyclohexyl)-6-(2,2,2-trifluoro-ethoxy)-nicotinamide and pharmaceutically acceptable salts thereof.

The compound of formula I can be prepared by a process, which process comprises coupling a compound of formula II,

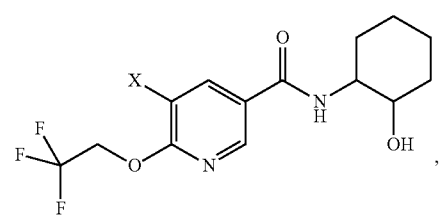

wherein X is halogen, with an aryl metal species of formula III,

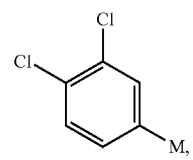

wherein M means boronic acid or a boronic acid ester, in the presence of a Pd catalyst under basic conditions, and optionally separating the isomers on a chiral HPLC column, and, if desired, converting the resulting compound of formula I into a pharmaceutically acceptable salt thereof.

The aryl metal species is preferably an aryl boronic acid or arylboronic acid ester. The palladium catalyst is preferably a palladium(II)acetate/triphenylphosphine mixture or a palladium(II)chloride-dppf complex which is used in the presence of a base, preferably triethylamine or sodium carbonate. X is halogen, more preferably X is bromo or iodo.

The synthesis of the compounds with the general structure I can be accomplished according to the following schemes 1 to 2.

Following the procedure according to scheme 1, compound AA (5-bromo-6-chloro-3-pyridinecarboxylic acid, CAS RN 29241-62-1) can be used as the starting material. AA is commercially available or can alternatively be prepared by a multi step sequence from 6-hydroxy-3-pyridinecarboxylic acid following literature procedures.

Compound AC can be prepared from AA by reaction with a suitably substituted primary or secondary alcohol of formula AB in the presence of a base, for example potassium hydroxide, in a inert solvent, for example dimethylsulfoxide, at temperatures from room temperature to reflux temperature of the solvent, preferably at room temperature.

Compound AE can be prepared by coupling AC and the corresponding amine of formula AD by suitable amide bond forming reactions. These reactions are known in the art. For example coupling reagents like N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), and O-benzotriazol-1-yl-N,N,N',N'-tetramethyluronium tetrafluoroborate (TBTU) can be employed to affect such transformation. A convenient method is to use for example TBTU and a base, for example Hünig's base (N-ethyldiisopropylamine) in an inert solvent such as for example dimethylformamide at room temperature.

In the following step compounds of formula I are obtained by coupling a suitably substituted aryl metal species of formula AF, preferably a arylboronic acid or arylboronic acid ester, with AE in the presence of a suitable catalyst, preferably a palladium catalyst and more preferably palladium(II)acetate/triphenylphosphine mixtures or palladium(II)chloride-dppf (1,1'-bis(diphenylphosphino)ferrocene) complexes and a base, preferably triethylamine or sodium carbonate in an inert solvent such as dimethylformamide or toluene.

Compounds of formula AE or compounds I that are prepared according to scheme 1 may contain one or more chiral centers depending on the exact nature of the amine AD. Chiral compounds AE-chiral or I-chiral may be obtained by a variety of methods known in the art, like synthesis from chiral precursors or chiral separation methods. Chiral separation on chiral HPLC columns is advantageously performed for the compound that provides the higher solubility in the mobile phase. Compounds of formula AE are in general more soluble in heptane/alcohol mixtures than compounds of formula I. The separation of AE-chiral 1 and AE-chiral 2 from AE-rac can be performed according to scheme 2 using a suitable chiral HPLC column such as ChiralPak AD® or similar stationary phases either in batch or as moving bed process with suitable mobile phases such as heptane/isopropanol mixtures.

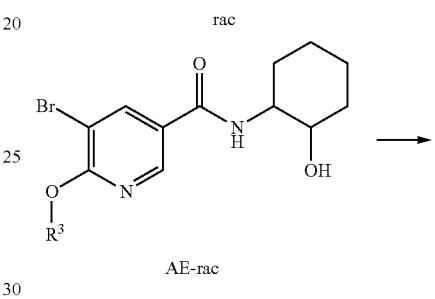

Scheme 2

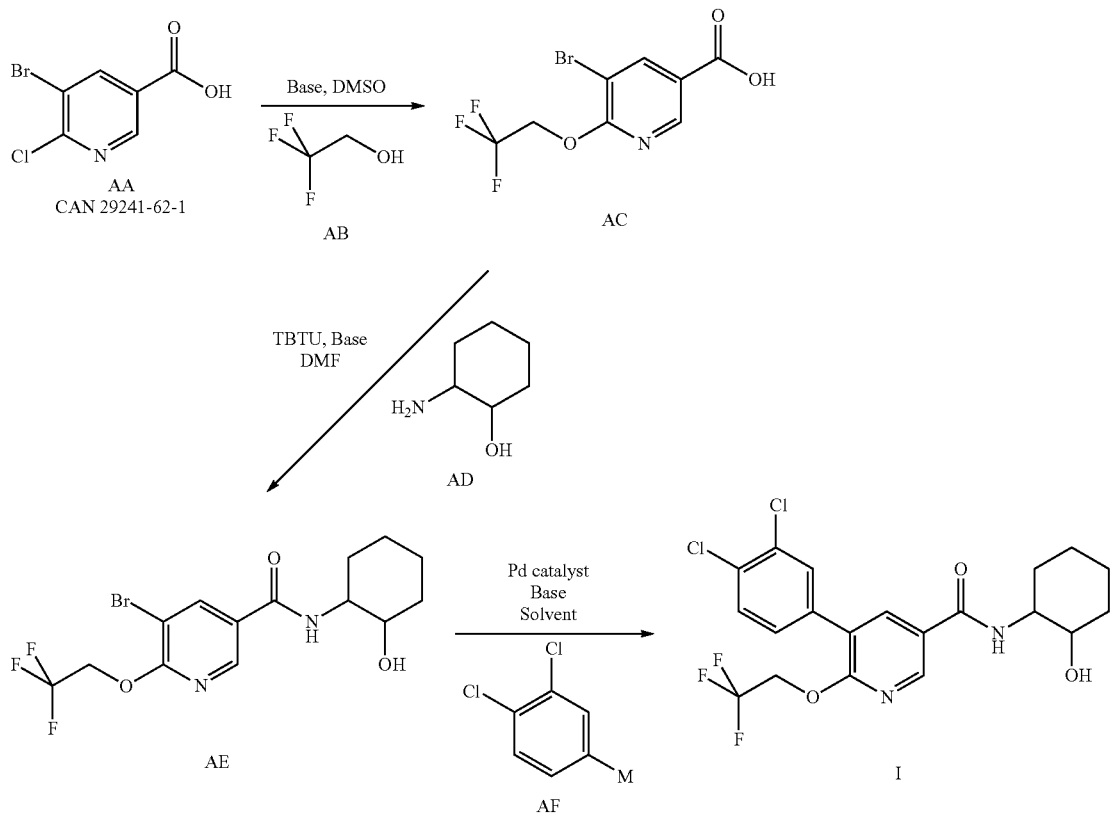

Scheme 1

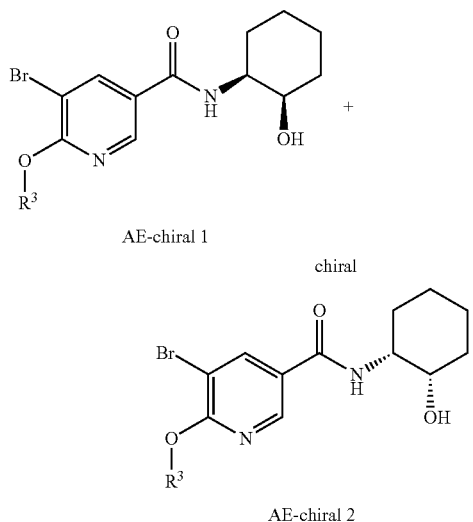

AE-chiral 1

AE-chiral 2

As described above, the compounds of formula I of the present invention can be used as medicaments for the treatment and/or prophylaxis of diseases which can be treated with HDL-cholesterol raising agents. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular diseases such as angina, ischemia, cardiac ischemia, stroke, myocardial infarction, reperfusion injury, angioplastic restenosis, hypertension, and vascular complications of diabetes, obesity or endotoxemia. The use as medicament for the treatment and/or prevention of dyslipidemia atherosclerosis and cardiovascular diseases is preferred.

The invention therefore also relates to a pharmaceutical composition comprising a compound as defined above and a pharmaceutically acceptable carrier and/or adjuvant which are useful for the treatment and/or prophylaxis of diseases which can be treated with HDL-cholesterol raising agents.

Thus, the invention relates to a pharmaceutical composition as defined above for the treatment and/or prophylaxis of atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular diseases such as angina, ischemia, cardiac ischemia, stroke, myocardial infarction, reperfusion injury, angioplastic restenosis, hypertension, and vascular complications of diabetes, obesity or endotoxemia.

In another embodiment, the invention relates to a method for the treatment and/or prophylaxis of diseases which can be treated with HDL-cholesterol raising agents, which method comprises administering a therapeutically effective amount of a compound of formula I to a patient in need thereof. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular diseases such as angina, ischemia, cardiac ischemia, stroke, myocardial infarction, reperfusion injury, angioplastic restenosis, hypertension, and vascular complications of diabetes, obesity or endotoxemia. A method for the treatment and/or prophylaxis of dyslipidemia atherosclerosis and cardiovascular diseases is preferred.

In addition, the invention relates to the use of compounds of formula I as defined above for the preparation of a medicament for the treatment and/or prophylaxis of diseases can be treated with HDL raising agents. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular diseases such as angina, ischemia, cardiac ischemia, stroke, myocardial infarction, reperfusion injury, angioplastic restenosis, hypertension, and vascular complications of diabetes, obesity or endotoxemia. The use of compounds of formula I as defined above for the preparation of medicaments for the treatment and/or prophylaxis of dyslipidemia atherosclerosis and cardiovascular diseases is preferred.

In addition, HDL raising agents of formula I are useful in combination or association with another compound, said compound being selected from the group consisting of an HMG-CoA reductase inhibitor, an microsomal triglyceride transfer protein (MTP)/ApoB secretion inhibitor, a PPAR activator, a cholesteryl ester transfer protein (CETP) inhibitor, a bile acid reuptake inhibitor, a cholesterol absorption inhibitor, a cholesterol synthesis inhibitor, a fibrate, niacin, a preparation containing niacin or other HM74a agonists, an ion-exchange resin, an antioxidant, an ACAT inhibitor or a bile acid sequestrant.

The invention therefore also relates to a pharmaceutical composition comprising a compound of formula I as defined above in combination or association with a compound selected from the group consisting of an HMG-CoA reductase inhibitor, an microsomal triglyceride transfer protein (MTP)/ApoB secretion inhibitor, a PPAR activator, a cholesteryl ester transfer protein (CETP) inhibitor, a bile acid reuptake inhibitor, a cholesterol absorption inhibitor, a cholesterol synthesis inhibitor, a fibrate, niacin, a preparation containing niacin or other HM74a agonists, an ion-exchange resin, an antioxidant, an ACAT inhibitor or a bile acid sequestrant, as well as a pharmaceutically acceptable carrier and/or adjuvant.

The invention further relates to the use of compounds of formula I as defined above in combination or association with a compound selected from the group consisting of an HMG-CoA reductase inhibitor, an microsomal triglyceride transfer protein (MTP)/ApoB secretion inhibitor, a PPAR activator, a cholesteryl ester transfer protein (CETP) inhibitor, a bile acid reuptake inhibitor, a cholesterol absorption inhibitor, a cholesterol synthesis inhibitor, a fibrate, niacin, a preparation containing niacin or other HM74a agonists, an ion-exchange resin, an antioxidant, an ACAT inhibitor or a bile acid sequestrant for the preparation of a medicament for the treatment and/or prophylaxis of diseases such as atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia.

The invention also relates to a method for the treatment and/or prophylaxis of diseases which can be treated with HDL-cholesterol raising agents, which method comprises administration of a therapeutically effective amount of a compound according to formula I in combination or association with a therapeutically effective amount of a compound selected from the group consisting of an HMG-CoA reductase inhibitor, an microsomal triglyceride transfer protein (MTP)/ApoB secretion inhibitor, a PPAR activator, a cholesteryl ester transfer protein (CETP) inhibitor, a bile acid reuptake inhibitor, a cholesterol absorption inhibitor, a cholesterol synthesis inhibitor, a fibrate, niacin, a preparation containing niacin or other HM74a agonists, an ion-exchange resin, an antioxidant, an ACAT inhibitor or a bile acid sequestrant.

The compounds of formula I and/or their pharmaceutically acceptable salts can be used in the form of pharmaceutical compositions for enteral, parenteral or topical administration. They can be administered, for example, perorally, e.g. in the form of tablets, coated tablets, dragées, hard and soft gelatine capsules, solutions, emulsions or suspensions, orally, e.g. in the form of buccal cavities, rectally, e.g. in the form of suppositories, parenterally, e.g. in the form of injection solutions or infusion solutions for intramuscular, intravenous or subcutaneous injection, or topically, e.g. in the form of ointments, creams or oils. Oral administration is preferred.

The production of the pharmaceutical compositions can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The therapeutically effective amount or dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 100 mg, especially about 1 to 50 mg, comes into consideration. Depending on severity of the disease and the precise pharmacokinetic profile the compound could be administered with one or several daily dosage units, e.g. in 1 to 3 dosage units.

The pharmaceutical compositions conveniently contain about 1-100 mg, preferably 5-50 mg, of a compound of formula I.

In the following examples the tests that were carried out in order to determine the activity of the compounds of formula I and especially their valuable pharmacological properties are described.

EXAMPLES

MS=mass spectrometry; EI=electron impact; ISP=ion spray, corresponds to ESI (electrospray); NMR data are reported in parts per million (δ) relative to internal tetramethylsilane and are referenced to the deuterium lock signal from the sample solvent ($d_6$-DMSO unless otherwise stated); coupling constants (J) are in Hertz, mp=melting point; bp=boiling point; HPLC=LC=high performance liquid chromatography, Rt=retention time, TLC=thin layer chromatography, RT=room temperature, TBTU=O-(Benzotriazol-1-yl)-N,N',N'-tetramethyl-uronium-tetrafluoroborate; DMF=dimethylformamide, DMSO=dimethylsulfoxide, THF=tetrahydrofurane, CAN=CAS Registry Number.

Example 1

Effects on Plasma Lipid Levels in Hamsters

Efficacy of compounds in modulating plasma lipid levels was determined in hamsters after 5 days of daily administration of compounds. Male hamsters of 6-8 weeks of age were used in the studies. After one week of acclimation, blood samples were collected from 4 hour-fasted animals for plasma lipid determination. Animals were then assigned to treatment groups based on HDL-cholesterol levels. Compounds were administered by gavage, once daily for five days. Control animals received vehicle alone. Blood was collected on day five from 4 hour-fasted hamsters, 2 hours after a final treatment, for plasma lipid analysis. Total cholesterol, HDL-cholesterol, LDL-cholesterol, and triglycerides were determined using colorimetric enzymatic assays (Roche Diagnostic GmbH, Mannheim, Germany). HDL-cholesterol was also determined after selective precipitation of HDL from plasma by standard procedures.

TABLE 1

Effects on HDL cholesterol levels in hamsters

| Compound | HDL Cholesterol levels [as % compared to control] @ 30 mg/kg p.o. of compound |
|---|---|
| 5-(3,4-Dichloro-phenyl)-N-((1R,2R)-2-hydroxy-cyclohexyl)-6-(2,2,2-trifluoro-ethoxy)-nicotinamide | +77.9 ± 11.1% |
| 5-(3,4-Dichloro-phenyl)-N-((1S,2R)-2-hydroxy-cyclohexyl)-6-(2,2,2-trifluoro-ethoxy)-nicotinamide | +121.9 ± 21.0% |
| 5-(4-Chloro-phenyl)-N-((1R,2R)-2-hydroxy-cyclohexyl)-6-(2,2,2-trifluoro-ethoxy)-nicotinamide | +103.8 ± 14.7% |

Example 2

CB1 and CB2 Receptor Affinity

The affinity of the compounds of the invention for cannabinoid receptors was determined using membrane preparations of human embryonic kidney (HEK) cells in which the human cannabis CB1 receptor is transiently transfected using the Semliki Forest Virus system in conjunction with [3H]-CP-55, 940 as radioligand. After incubation of freshly prepared cell membrane preparation with the [3H]-ligand, with or without addition of compounds of the invention, separation of bound and free ligand was performed by filtration over glass fiber filters. Radioactivity on the filter was measured by scintillation counting.

The affinity of the compounds of the invention for cannabinoid CB2 receptors was determined using membrane preparations of human embryonic kidney (HEK) cells in which the human cannabis CB2 receptor is transiently transfected using the Semliki Forest Virus system in conjunction with [3H]-CP-55,940 as radioligand. After incubation of freshly prepared cell membrane preparation with the [3H]-ligand, with or without addition of compounds of the invention, separation of bound and free ligand was performed by filtration over glass fiber filters. Radioactivity on the filter was measured by scintillation counting.

$K_i$ values were calculated from the $IC_{50}$ using the Cheng-Prusoff equation.

TABLE 2

CB1 and CB2-receptor affinity

| Compound | CB1 receptor affinity [$K_i$ in μM] | CB2 receptor affinity [$K_i$ in μM] |
|---|---|---|
| 5-(3,4-Dichloro-phenyl)-N-((1R,2R)-2-hydroxy-cyclohexyl)-6-(2,2,2-trifluoro-ethoxy)-nicotinamide | 1.3 | >10 |
| 5-(3,4-Dichloro-phenyl)-N-((1S,2R)-2-hydroxy-cyclohexyl)-6-(2,2,2-trifluoro-ethoxy)-nicotinamide | >10 | >10 |
| 5-(4-Chloro-phenyl)-N-((1R,2R)-2-hydroxy-cyclohexyl)-6-(2,2,2-trifluoro-ethoxy)-nicotinamide | 0.028 | >10 |

Example 3

Preparation of 5-(3,4-dichloro-phenyl)-N-((1R,2R)-2-hydroxy-cyclohexyl)-6-(2,2,2-trifluoro-ethoxy)-nicotinamide

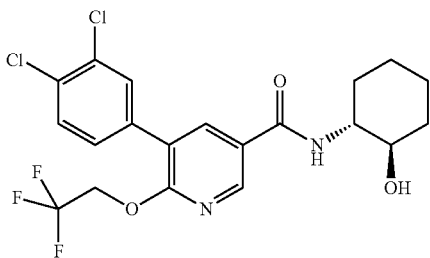

a) 5-Bromo-6-(2,2,2-trifluoro-ethoxy)-nicotinic acid

5-Bromo-6-chloro-3-pyridinecarboxylic acid (68.0 g, 0.288 mol, CAN 29241-62-1) was dissolved in DMSO (1000 mL). To this solution was added with stirring potassium hydroxide (48.25 g, 0.86 mol) and after 10 minutes of stirring at room temperature 2,2,2-trifluoroethanol (26.9 mL, 0.374 mol) was added. The mixture was stirred at room temperature for 24 h. Water (1000 mL) and concentrated hydrochloric acid (107 mL, 1280 mmol, 37%) was added and the suspension was stirred vigorously for 4 hours. The precipitate was filtered, washed with water (4×100 mL) and vacuum dried over night to give the title compound (80.4 g) as an off white solid; MS (EI) 299, 301 (M)⁺.

b) 5-Bromo-N-((1R,2R)-2-hydroxy-cyclohexyl)-6-(2,2,2-trifluoro-ethoxy)-nicotinamide 5-Bromo-6-(2,2,2-trifluoro-ethoxy)-nicotinic acid (50.0 g, 0.166 mol) was dissolved in DMF (600 mL). To the solution was added TBTU (58.9 g, 0.183 mol), N,N-diisopropylethyl amine (142.6 mL, 0.83 mol) and (1R,2R)-2-amino-cyclohexanol (21.1 g, 0.183 mol). The reaction mixture was stirred for 3 h at room temperature. The solvent was evaporated in vacuo, the residue was dissolved in a mixture of ethyl acetate (1200 mL) and THF (300 mL). The solution was washed twice with water (700 mL) and the water phases were extracted with ethyl acetate (600 mL). Organic phases were pooled, dried with MgSO4 and concentrated to about 900 mL. The product precipitated upon stirring and cooling to 0° C. Filtration, washing with ethyl acetate/n-heptane (1:1) and drying in vacuo gave the title compound (53.1 g) as a white solid; MS (ISP) 397, 399 (M)⁺.

c) 5-(3,4-dichloro-phenyl)-N-((1R,2R)-2-hydroxy-cyclohexyl)-6-(2,2,2-trifluoro-ethoxy)-nicotinamide 5-Bromo-N-((1R,2R)-2-hydroxy-cyclohexyl)-6-(2,2,2-trifluoro-ethoxy)-nicotinamide (59.8 g, 151 mmol) was dissolved in toluene (2500 mL) and DMF (200 mL). To this solution was added with stirring [1,1'-bis(diphenylphosphino)ferrocene]-dichloropalladium(II) CH₂Cl₂ (6.15 g, 7.5 mmol), 3,4-dichlorophenylboronic acid (30.2 g, 158 mmol) and sodium carbonate solution (2M, 150 mL). This mixture was heated to 90° C. for 2 h, cooled to room temperature and filtered through diatomaceous earth. The filter cake was thoroughly washed with ethyl acetate (3000 mL). The filtrates were combined, washed twice with water (2×2000 mL), and the water phases were extracted with ethyl acetate (2×1500 mL). Organic phases were pooled, dried with MgSO4 and the volatiles removed in vacuo. The residue was purified by filtration through silica (500 g) with ethyl acetate. The solvent was removed and the residue was triturated with diethyl ether to give after drying in vacuo the title compound (45.6 g) as a grayish solid; MS 463.079, 465.077 (M+H)⁺.

Example 4

Preparation of 5-(3,4-Dichloro-phenyl)-N-((1S,2R)-2-hydroxy-cyclohexyl)-6-(2,2,2-trifluoro-ethoxy)-nicotinamide

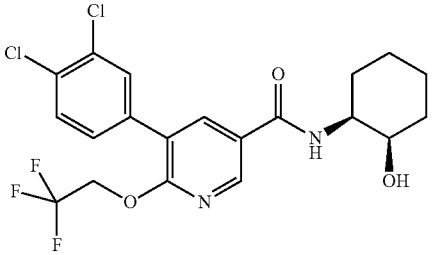

a) 5-Bromo-N-((1SR,2RS)-2-hydroxy-cyclohexyl)-6-(2,2,2-trifluoro-ethoxy)-nicotinamide 5-Bromo-6-(2,2,2-trifluoro-ethoxy)-nicotinic acid (75.0 g, 0.25 mol) was dissolved in DMF (850 mL). To the solution was added TBTU (91.0 g, 0.275 mol), N,N-diisopropylethyl amine (214 mL, 1.25 mol) and (1SR,2RS)-2-amino-cyclohexanol hydrochloride (41.7 g, 0.275 mol). The reaction mixture was stirred for 1.5 h at room temperature. The solvent was evaporated in vacuo, the residue was partitioned between ethyl acetate (2500 mL) and 1 N sodium hydroxide solution (2000 mL), the water phase was separated, extracted once more with ethyl acetate (1000 mL) and the organic phases were washed 2 times with water (2×1500 mL). Organic phases were pooled, dried with MgSO4 and concentrated to about 900 mL. The product precipitated upon stirring and cooling to 0° C. Filtration, washing with ethyl acetate/n- heptane (1:1) and drying in vacuo gave the title compound (81.1 g) as a white solid; MS (ISP) 397, 399 (M)⁺.

b) 5-Bromo-N-((1S,2R)-2-hydroxy-cyclohexyl)-6-(2, 2,2-trifluoro-ethoxy)-nicotinamide 5-Bromo-N-((1SR,2RS)-2-hydroxy-cyclohexyl)-6-(2,2, 2-trifluoro-ethoxy)-nicotinamide (91.3 g, 0.23 mol) was submitted to preparative HPLC on ChiralPak AD® (250×110 mm column) using n-heptane/isopropanol 85/15 as mobile phase. Baseline separation was achieved and the title compound (43.6 g) was isolated as colorless solid from the first peak; MS (ISP) 395.2, 397.2 (M−H); ORD (589 nM, 20° C., CHCl₃) −21.6°.

c) 5-(3,4-Dichloro-phenyl)-N-((1S,2R)-2-hydroxy-cyclohexyl)-6-(2,2,2-trifluoro-ethoxy)-nicotinamide 5-Bromo-N-((1S,2R)-2-hydroxy-cyclohexyl)-6-(2,2,2-trifluoro-ethoxy)-nicotinamide (42.0 g, 106 mmol) was dissolved in toluene (1900 mL) and DMF (100 mL). To this solution was added with stirring [1,1'-bis(diphenylphosphino)ferrocene]-dichloropalladium(II) CH₂Cl₂ (0.9 g, 1.06 mmol), 3,4-dichlorophenylboronic acid (20.2 g, 106 mmol) and sodium carbonate solution (2M, 106 mL). This mixture was heated to 90° C. for 2 h, cooled to room temperature and partitioned between ethyl acetate (1000 mL) and water (2000 mL), the water phase was separated, extracted twice more with ethyl acetate (2×1000 mL) and the organic phases were washed once with water and once with brine (1000 mL each). Organic phases were pooled, dried with MgSO4 and the volatiles removed in vacuo. The residue was dissolved in diethyl ether (500 mL) and filtered through diatomaceous earth. The title compound precipitated when n-heptane (500 mL) was added drop wise to the diethyl ether solution, was filtered off and dried in vacuo to give 33.3 g the title compound as an off-white solid; MS 463.079 (M+H)⁺.

Example 5

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example 6

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 7

Injection solutions can have the following composition:

| | |
| --- | --- |
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

The invention claimed is:
1. A compound of formula I,

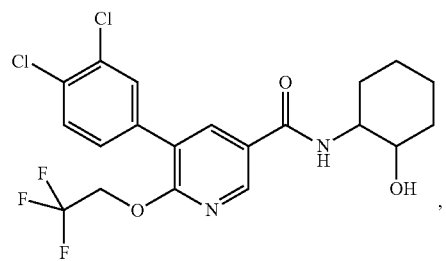

or an isomeric form or pharmaceutically acceptable salt thereof.

2. A compound according to claim 1, wherein the compound is 5-(3,4-dichloro-phenyl)-N-((1R,2R)-2-hydroxy-cyclohexyl)-6-(2,2,2-trifluoro-ethoxy)-nicotinamide.

3. A compound according to claim 1, wherein the compound is 5-(3,4-dichloro-phenyl)-N-((1S,2R)-2-hydroxy-cyclohexyl)-6-(2,2,2-trifluoro-ethoxy)-nicotinamide.

4. A pharmaceutical composition comprising a compound according to claim 1 and a pharmaceutically acceptable carrier and/or an adjuvant.

* * * * *